(12) United States Patent
Davis et al.

(10) Patent No.: US 7,041,793 B2
(45) Date of Patent: *May 9, 2006

(54) DETERGENT COMPOSITIONS COMPRISING BENEFIT AGENTS

(75) Inventors: Paul James Davis, Shambrook (GB); Neil James Parry, Shambrook (GB)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 167 days.

This patent is subject to a terminal disclaimer.

(21) Appl. No.: 09/998,660

(22) Filed: Nov. 29, 2001

(65) Prior Publication Data

US 2002/0155972 A1 Oct. 24, 2002

Related U.S. Application Data

(62) Division of application No. 09/742,690, filed on Dec. 20, 2000.

(30) Foreign Application Priority Data

Dec. 22, 1999 (EP) .................................. 99310428

(51) Int. Cl.
- C11D 3/00 (2006.01)
- C11D 7/42 (2006.01)
- C07K 1/00 (2006.01)
- C12N 9/00 (2006.01)
- C12N 9/24 (2006.01)

(52) U.S. Cl. .............................. 530/350; 435/4; 435/6; 435/69.1; 435/183; 435/200; 435/209; 435/86; 510/114; 510/392; 510/515

(58) Field of Classification Search ................ 435/183, 435/200, 209, 4, 6, 69.1, 86; 530/350; 436/86; 510/114, 392, 515
See application file for complete search history.

(56) References Cited

U.S. PATENT DOCUMENTS

| | | | | |
|---|---|---|---|---|
| 5,190,661 | A | 3/1993 | Bruening et al. | 210/670 |
| 5,500,153 | A | 3/1996 | Figueroa et al. | 252/548 |
| 5,652,206 | A | 7/1997 | Bacon et al. | 510/101 |
| 5,686,014 | A | 11/1997 | Baillely et al. | 252/186.33 |
| 5,719,044 | A * | 2/1998 | Shoseyov et al. | 435/69.7 |
| 6,579,842 | B1 * | 6/2003 | Howell et al. | 510/392 |
| 6,586,384 | B1 * | 7/2003 | Hemmington et al. | 510/392 |
| 2001/0039250 | A1 * | 11/2001 | Howell et al. | 510/130 |

FOREIGN PATENT DOCUMENTS

| | | |
|---|---|---|
| DE | 195 36 714 | 4/1997 |
| DE | 196 21 224 | 11/1997 |
| EP | 0 385 529 | 9/1990 |
| EP | 385 529 | 9/1990 |
| WO | WO 94/07998 * | 4/1994 |
| WO | 94/25591 | 11/1994 |
| WO | 95/02675 | 1/1995 |
| WO | 95/09909 | 4/1995 |
| WO | 98/00500 | 1/1998 |
| WO | 98/01523 | 1/1998 |
| WO | 98/06812 | 2/1998 |
| WO | 98/07820 | 2/1998 |
| WO | 98/23716 | 6/1998 |
| WO | 98/56885 | 12/1998 |
| WO | 99/02693 | 1/1999 |
| WO | 99/12624 | 3/1999 |
| WO | 99/23221 | 5/1999 |
| WO | 99/36436 | 7/1999 |
| WO | 99/36469 | 7/1999 |
| WO | 99/57154 | 11/1999 |
| WO | 99/57155 | 11/1999 |
| WO | 99/57250 | 11/1999 |
| WO | 00/18864 | 4/2000 |
| WO | 00/36094 | 6/2000 |
| WO | 01/07555 | 2/2001 |
| WO | 01/16269 | 3/2001 |

OTHER PUBLICATIONS

PCT International Search Report in a PCT application PCT/EP 00/12523.
PCT International Search Report in a PCT application PCT/EP 00/12529.
PCT International Search Report in a PCT application PCT/EP 00/12530.
PCT International Search Report on a PCT application PCT/EP 00/12531.
PCT International Search Report in a PCT application PCT/EP 00/12532.
Co-pending application: U.S. Appl. No. 09/742,693; filed—Dec. 20, 2000, Howell et al.
Co-pending application: U.S. Appl. No. 09/742,694; filed—Dec. 20, 2000, Hemington et al.
Co-pending application: U.S. Appl. No. 09/472,689; filed—Dec. 20, 2000, Howell et al.
Co-pending application; U.S. Appl. No. 09/742,692; filed—Dec. 20, 2000, Antheunisse et al.
Co-pending application; U.S. Appl. No. 09/712,561; filed—Nov. 14, 2000, Berry et al.
PCT International Search Report in a PCT application PCT/EP 00/12523.
PCT International Search Report in a PCT application PCT/EP 00/12529.

(Continued)

Primary Examiner—Manjunath N. Rao
(74) Attorney, Agent, or Firm—Rimma Mitelman

(57) ABSTRACT

Detergent composition comprising fusion protein comprising a cellulose binding domain and a domain having a high binding affinity for another ligand. Preferably, the domain having a high binding affinity is directed at a Benefit Agent.

8 Claims, 4 Drawing Sheets

OTHER PUBLICATIONS

PCT International Search Report in a PCT application PCT/EP 00/12530.

PCT International Search Report in a PCT application PCT/EP 00/12531.

PCT International Search Report in a PCT application PCT/EP 00/12532.

Co-pending application: U.S. Appl. No. 09/742,693; filed—Dec. 20, 2000, Howell et al.

Co-pending application: U.S. Appl. No. 09/742,694; filed—Dec. 20, 2000, Hemmington et al.

Co-pending application: U.S. Appl. No. 09/742,689; filed—Dec. 20, 2000, Howell et al.

Co-pending application; U.S. Appl. No. 09/742,692; filed—Dec. 20, 2000, Antheunisse et al.

Co-pending application; U.S. Appl. No. 09/712,561; filed—Nov. 14, 2000, Berry et al.

* cited by examiner

```
                                          PstI
            E   K   R   Q   V   Q   L   Q   E   S   G   G   G   L   V   Q
  1    TCGAGAAAAG ACAGGTGCAG CTGCAGGAGT CAGGGGGAGG ATTGGTGCAG

A   G   G   S   L   R   L   S   C   A   A   S   G   R   A   T   S
 51    GCTGGGGGCT CTCTGAGACT CTCCTGTGCA GCCTCGGGAC GCGCCACCAG

G   H   G   H   Y   G   M   G   W   F   R   Q   V   P   G   K
101    TGGTCATGGT CACTATGGTA TGGGCTGGTT CCGCCAGGTT CCAGGGAAGG

E   R   E   F   V   A   A   I   R   W   S   G   K   E   T   W   Y
151    AGCGTGAGTT TGTCGCAGCT ATTAGGTGGA GTGGTAAAGA GACATGGTAT

K   D   S   V   K   G   R   F   T   I   S   R   D   N   A   K   T
201    AAAGACTCCG TGAAGGGCCG ATTCACCATC TCCAGAGATA ACGCCAAGAC

T   V   Y   L   Q   M   N   S   L   K   P   E   D   T   A   V
251    TACGGTTTAT CTGCAAATGA ACAGCCTGAA ACCTGAAGAT ACGGCCGTTT

Y   Y   C   A   A   R   P   V   R   V   D   D   I   S   L   P   V
301    ATTATTGTGC CGCTCGACCG GTCCGCGTGG ATGATATTTC CCTGCCGGTT

G   F   D   Y   W   G   Q   G   T   Q   V   T   V   S   S   G   S
351    GGGTTTGACT ACTGGGGCCA GGGGACCCAG GTCACCGTCT CCTCAGGATC

BamHI
                                                        linker
            H   H   H   H   H   H   G   S   T   S   I   E   G   R   T   Q
401    TCATCACCAT CACCATCACG GATCCACCTC CATTGAAGGT CGTACCCAGT S   H   Y   G   Q   C   G   G   I   G   Y   S   G   P   T   V   C
451    CTCACTACGG TCAGTGTGGT GGTATTGGTT ACTCCGGTCC AACCGTCTGT A   S   G   T   T   C   Q   V   L   N   P   Y   Y   S   Q   C   L
501    GCCTCTGGTA CCACCTGTCA GGTTCTGAAC CCTTACTACT CCCAGTGTCT

*   *
551    GTAATAAG
```

DETERGENT COMPOSITIONS COMPRISING BENEFIT AGENTS

This application a divisional application of Ser. No. 09/742,690 filed Dec. 20, 2000.

TECHNICAL FIELD

The present invention generally relates to detergent compositions comprising benefit agents. More in particular, it relates to detergent compositions comprising fusion proteins which are useful for delivering a benefit agent to a fabric.

BACKGROUND AND PRIOR ART

WO-A-98/00500 (Unilever) discloses detergent compositions wherein a Benefit Agent is delivered onto fabric by means of peptide or protein Deposition Aid having a high affinity for fabric. The Benefit Agent can be a fabric softening agent, a perfume, a polymeric lubricant, a photoprotective agent, a latex, a resin, a dye fixative agent, an encapsulated material, an antioxidant, an insecticide, a soil repelling agent or a soil release agent. The Benefit Agent is attached or adsorbed to a peptide or protein Deposition Aid having a high affinity for fabric. Preferably, the deposition aid is the cellulose binding domain of a cellulase enzyme. The compositions are said to effectively deposit the Benefit Agent onto the fabric during the wash cycle.

The detergent compositions disclosed in WO-A-98/00500 have a number of drawbacks. The Benefit Agent has to be attached/adsorbed to the Deposition Aid. If it is to be attached, it is preferably done by means of a linking agent. However, not all benefit agents can be derivatised. Furthermore, linking the Benefit Agent to the Deposition Aid may negatively affect the properties of the Benefit Agent. For example, perfumes cannot be covalently bound to larger molecules without negatively affecting their perfume properties.

It is therefore an object of the present invention to provide an alternative or improved detergent composition which is capable of delivering a benefit agent to a fabric during a washing or rinsing process.

Surprisingly, we have now found that these and other objects of the invention may be achieved by the detergent compositions of the present invention, which are characterised in that they comprise a fusion protein comprising a cellulose binding domain and a domain having a high binding affinity for another ligand. This fusion molecule is bi-functional in its binding ability, whereby the cellulose binding domain region binds to cellulosic based materials and the second domain binds to another ligand.

According to DE-A-196 21 224 (Henkel), the transfer of textile dyes from one garment to another during a washing or rinsing process may be inhibited by adding antibodies against the textile dye to the wash or rinse liquid.

WO-A-98/07820 (P&G) discloses rinse treatment compositions containing antibodies directed at cellulase and standard softener actives (such as DEQA).

DEFINITION OF THE INVENTION

According to a first aspect of the invention, there is provided a fusion protein comprising a cellulose binding domain and a domain having a high binding affinity for another ligand. Preferably, the domain having a high binding affinity is directed at a Benefit Agent.

According to a second aspect, there is provided a detergent composition comprising said fusion protein.

According to a third aspect, there is provided a process for delivering a benefit agent to a fabric by treating said fabric with a composition comprising said fusion protein and a benefit agent.

BRIEF DESCRIPTION OF THE DRAWINGS

FIG. 1 shows the gene SEQ ID. NO: 1 (sequence 1-558) and the produced protein SEQ ID. NO: 2 as further described in Example 4.

DETAILED DESCRIPTION OF THE INVENTION

1.1 The Cellulose Binding Domain

Figure 2:
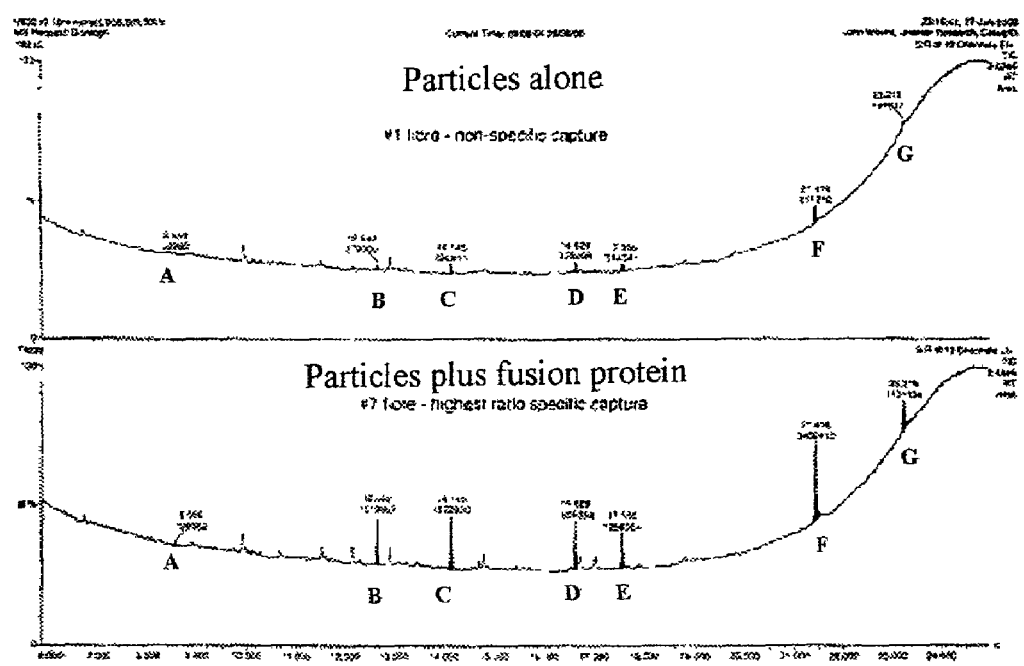
FIGS. 2, 3 and 4 illustrate results obtained from Examples 5 and 6 described in greater detail hereinbelow.
Figure 3:
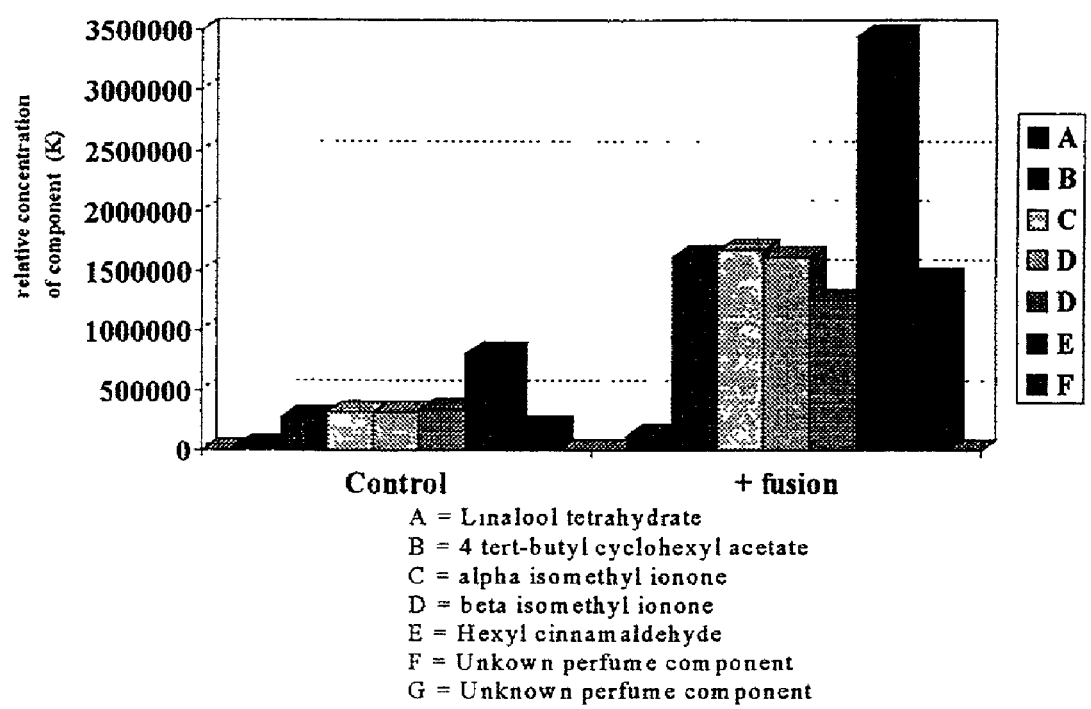
Figure 4:
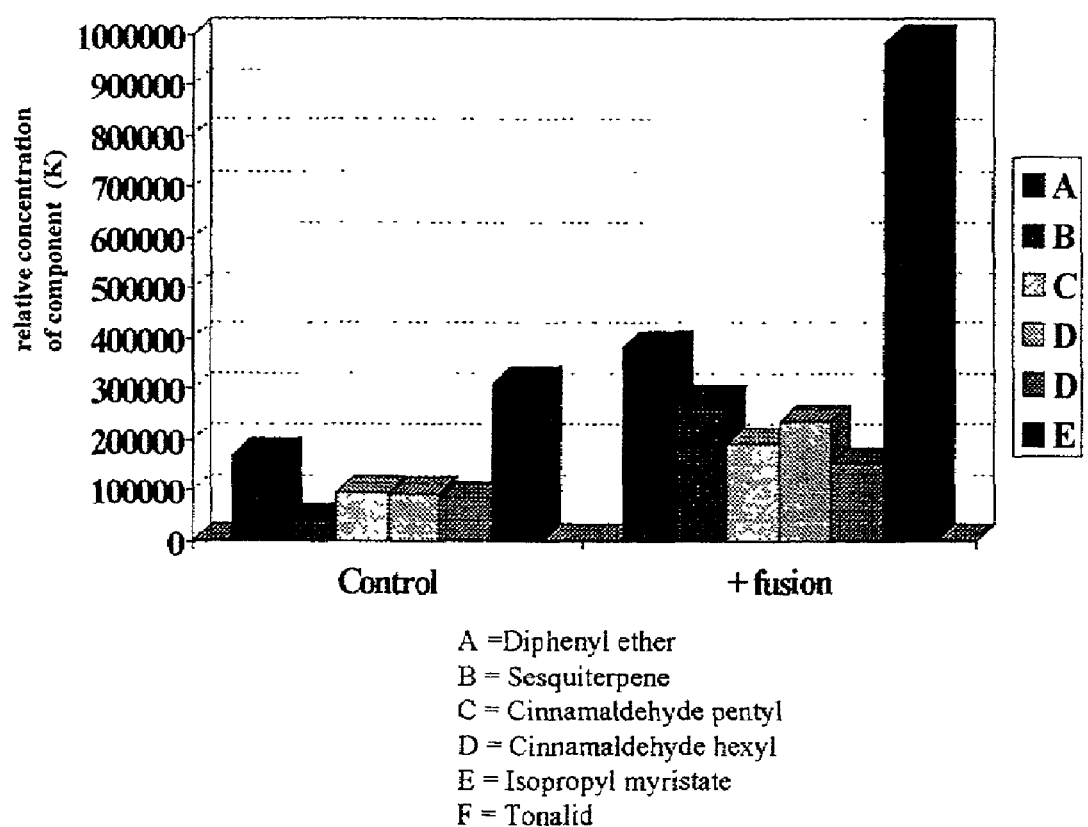

In its first aspect, the invention relates to a fusion protein comprising a cellulose binding domain (CBD) and a domain having a high binding affinity for another ligand. The cellulose binding domain is a part of most cellulase enzymes and can be obtained therefrom. Cellulose binding domains are also obtainable from xylanase and other hemicellulase degrading enzymes. Preferably, the cellulose binding domain is obtainable from a fungal enzyme origin such as Humicola, Trichoderma, Thermomonospora, Phanerochaete, Aspergillus or from a bacterial enzyme origin such as Bacillus, Clostridium, Streptomyces, Cellulomonas and Pseudomonas. Especially preferred is the cellulose binding domain which is obtainable from Trichoderma reesei.

In the fusion protein according to the invention, the cellulose binding domain is fused to a second domain having a high binding affinity for another ligand. Preferably, the cellulose binding domain is connected to the domain having a high binding affinity for another ligand by means of a linker consisting of about 0–20, preferably about 2–15, more preferably of 2–5 amino acid residues.

The second domain having a high binding affinity for another ligand may, for instance, be an antibody or an antibody fragment. Especially preferred are heavy chain antibodies such as found in Camelidae.

The fusion protein according to the invention may comprise more than two recognition domains. It is for example possible to produce a CBD fusion protein with more than one antibody domain, in which the antibody domains may bind to the same or bind to different antigens. Conversely, it is also possible in the CBD antibody fusion format to produce a molecule with one antibody domain with more than one CBD, whereby the CBD's incorporated may be identical sequences or from more than one source, or modified varieties thereof.

Generally speaking, the degree of binding of a molecule A to another molecule B can be generally expressed by the chemical equilibrium constant $K_d$ resulting from the following reaction:

$$[A]+[B] \Leftrightarrow [A\equiv B]$$

The chemical equilibrium constant $K_d$ is then given by:

$$K_d = \frac{[A]\times[B]}{[A\equiv B]}$$

Whether the binding of a molecule to the fabric/ligand is specific or not can be judged from the difference between the binding ($K_d$ value) of the molecule to one type of fabric/ligand, versus the binding to another type of fabric/ligand material. For applications in laundry, said ligand material will form part of or be associated with a benefit agent. In this aspect of the invention, the CBD region of the fusion protein binds to the fabric and the high affinity domain region binds to the benefit agent. Alternatively, this approach can be reversed whereby the fabric material, or a ligand bound to the fabric is targeted by the high affinity domain of the fusion protein and the cellulose binding domain region binds to a cellulosic based or cellulosic containing benefit agent. However, it will usually be more convenient to measure $K_d$ values and differences in $K_d$ values on other materials such as a polystyrene microtitre plate or a specialised surface in an analytical biosensor. The difference between the two binding constants should be minimally 10, preferably more than 100, and more preferably, more that 1000. Typically, the reagent should bind to the ligand/fabric, with a $K_d$ lower than $10^{-4}$ M, preferably lower than $10^{-6}$ M and could be $10^{-10}$ M or even less. Higher binding affinities ($K_d$ of less than $10^{-5}$ M) and/or a larger difference between the one type of ligand/fabric and another type of ligand/fabric (or background) binding would increase the deposition of the benefit agent. Also, the weight efficiency of the reagent in the total rinse composition would be increased and smaller amounts of the reagent would be required.

Several classes of reagent or molecules can be envisaged which deliver the capability of specific binding to fabrics/ligands, to which one would like to deliver the benefit agent. In the following we will give a number of examples of such molecules having such capabilities, without pretending to be exhaustive.

1.2.1. Antibodies.

Antibodies are specific binding proteins. Their function in nature is to protect against disease by recognising (and binding) foreign bodies, such as viruses or Bacteria, but not self-cells. Furthermore, methods are well-known in the art to generate antibodies that are specific for almost any protein, organic molecule, or cell surface, that is likely to be encountered. This binding specificity has been exploited in the Biotechnology industry, principally for medical diagnostics. For example, many home-based pregnancy test kits comprise an antibody that specifically binds to the pregnancy marker hormone, human chorionic gonadotropin (hCG), but not to other hormones present in urine.

More recently, the use of antibodies in laundry products has been described (Henkel, Procter and Gamble, Unilever). In particular, Unilever has described the use of stain-specific antibodies to target bleaching enzymes exclusively to stains but not to dyes—thus achieving efficient stain removal without damaging surrounding fabric.

Antibodies are well known examples of molecules which are capable of binding specifically to compounds against which they were raised. Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria.

A class of antibodies of particular interest is formed by the Heavy Chain antibodies as found in Camelidae, like the camel or the llama. The binding domains of these antibodies consist of a single polypeptide fragment, namely the variable region of the heavy chain polypeptide (HC-V). In contrast, in the classic antibodies (murine, human, etc.), the binding domain consists of two polypeptide chains (the variable regions of the heavy chain ($V_h$) and the light chain ($V_l$)). Procedures to obtain heavy chain immunoglobulins from Camelidae, or (functionalized) fragments thereof, have been described in WO-A-94/04678 (Casterman and Hamers) and WO-A-94/25591 (Unilever and Free University of Brussels).

Alternatively, binding domains can be obtained from the $V_h$ fragments of classical antibodies by a procedure termed "camelization". Hereby the classical $V_h$ fragment is transformed, by substitution of a number of amino acids, into a HC-V-like fragment, whereby its binding properties are retained. This procedure has been described by Riechmann et al. in a number of publications (J. Mol. Biol. (1996) 259, 957–969; Protein. Eng. (1996) 9, 531–537, Bio/Technology (1995) 13, 475–479). Also HC-V fragments can be produced through recombinant DNA technology in a number of microbial hosts (bacterial, yeast, mould), as described in WO-A-94/29457 (Unilever).

Methods for producing fusion proteins that comprise an enzyme and an antibody or that comprise an enzyme and an antibody fragment are already known in the art. One approach is described by Neuberger and Rabbits (EP-A-194 276). A method for producing a fusion protein comprising an enzyme and an antibody fragment that was derived from an antibody originating in Camelidae is described in WO-A-94/25591. A method for producing bispecific antibody fragments is described by Holliger et al. (1993) PNAS 90, 6444–6448.

A particularly attractive feature of antibody binding behaviour is their reported ability to bind to a "family" of structurally related molecules. For example, in Gani et al. (J. Steroid Biochem. Molec. Biol. 48, 277–282) an antibody is described that was raised against progesterone but also binds to the structurally-related steroids, pregnanedione, pregnanolone and 6-hydroxy-progesterone. Therefore, using the same approach, antibodies could be isolated that bind to a whole "family" of stain chromophores (such as the polyphenols, porphyrins, or caretenoids as described below). A broad action antibody such as this could be used to treat several different stains when coupled to a bleaching enzyme.

1.2.2. Peptides.

Peptides usually have lower binding affinities to the substances of interest than antibodies. Nevertheless, the binding properties of carefully selected or designed peptides can be sufficient to deliver the desired selectivity in an oxidation process. A peptide which is capable of binding selectively to a fabric/ligand to which one would like to deliver a benefit agent, can for instance be obtained from a protein which is known to bind to that specific fabric/ligand. An example of such a peptide would be a binding region extracted from an antibody raised against that fabric/ligand. A suitable peptide could be analogous to the active center of a protein analogous to a non-catalytic binding domain of a protein, e.g. a receptor.

Alternatively, peptides that bind to such substance can be obtained by the use of peptide combinatorial libraries. Such a library may contain up to $10^{10}$ peptides, from which the peptide with the desired binding properties can be isolated. (R. A. Houghten, Trends in Genetics, Vol 9, no &, 235–239). Several embodiments have been described for this procedure (J. Scott et al., Science (1990) 249, 386–390; Fodor et al., Science (1991) 251, 767–773; K. Lam et al., Nature (1991) 354, 82–84; R. A. Houghten et al., Nature (1991) 354, 84–86).

Suitable peptides can be produced by organic synthesis, using for example the Merrifield procedure (Merrifield (1963) J.Am.Chem.Soc. 85, 2149–2154). Alternatively, the peptides can be produced by recombinant DNA technology in microbial hosts (yeast, moulds, bacteria)(K. N. Faber et al. (1996) Appl. Microbiol. Biotechnol. 45, 72–79).

1.2.3. Peptidomimics.

In order to improve the stability and/or binding properties of a peptide, the molecule can be modified by the incorporation of non-natural amino acids and/or non-natural chemical linkages between the amino acids. Such molecules are called peptidomimics (H. U. Saragovi et al. (1991) Bio/Technology 10, 773–778; S. Chen et al. (1992) Proc.Natl.Acad. Sci. USA 89, 5872–5876). The production of such compounds is restricted to chemical synthesis.

1.2.4. Other Organic Molecules.

It can be readily envisaged that other molecular structures, which need not be related to proteins, peptides or derivatives thereof, can be found which bind selectively to fabrics/ligands to which one would like to deliver a benefit agent. For example, certain polymeric RNA molecules which have been shown to bind small synthetic dye molecules (A. Ellington et al. (1990) Nature 346, 818–822). Such binding compounds can be obtained by the combinatorial approach, as described for peptides (L. B. McGown et al. (1995), Analytical Chemistry, 663A–668A).

This approach can also be applied for purely organic compounds which are not polymeric. Combinatorial procedures for synthesis and selection for the desired binding properties have been described for such compounds (Weber et al. (1995) Angew.Chem.Int.Ed.Engl. 34, 2280–2282; G. Lowe (1995), Chemical Society Reviews 24, 309–317; L. A. Thompson et al. (1996) Chem. Rev. 96, 550–600). Once suitable binding compounds have been identified, they can be produced on a larger scale by means of organic synthesis.

A further embodiment would be for the domain with a high binding affinity to be a bispecific reagent. Such a reagent could fulfil the requirement of accumulating the benefit agent on the fabric either by supplying said reagent together with the benefit agent as a pre-formed non-covalent complex or by supplying the two separately and allowing them to self-assemble either in the wash liquor or on the fabric.

In the detergent composition according to the invention, the fusion protein can be used to deposit a Benefit Agent onto the fabric by means of the cellulose binding domain.

Alternatively, the domain having a high binding affinity for the fabric/ligand can be used to target the benefit agent.

In a further embodiment, the detergent compositions of the invention comprise micro-particles sensitised with CBD-antibody fusions, and configured such that the micro-particles are loaded with the benefit agent and the antibody domain of the fusion protein has a high affinity or specificity for a substance (or "marker molecule") typically found on some regions of fabrics but not on others. Examples of such marker molecules include bleach-damaged dyes and microbes known to be associated with malodour. The antibody domain targets the benefit agent to its intended site of action and binds it there. For example, Microbe-specific antibody based fusions may target fragrance-containing particles to the regions of malodour. Thus, a more efficient use of expensive ingredients is achieved. Alternatively, antibody based fusions specific for bleach-damaged dyes can target dyed particles to faded regions, thus replenishing the colour lost in the main wash cycle.

The CBD antibody fusion protein binds to the fabric via the CBD region, thereby allowing the antibody domain to bind to corresponding antigens/ligands that comprise or form part of the benefit agent. The fusion protein can be dosed in conjunction with the benefit agent or can be added to the fabric prior to the said fabric coming into contact with the benefit agent.

A further aspect of the invention is a process for delivering a benefit agent to a fabric, by treating said fabric with a composition comprising the fusion protein and a benefit agent. The benefit agent can be selected from softening agents, finishing agents/protective agents, fragrances (perfumes), bleaching agents.

Examples of softening agents are clays,-cationic surfactants or silicon compounds. Examples of finishing agents/protective agents are polymeric lubricants, soil repelling agents, soil release agents, photo-protective agents (sunscreens), anti-static agents, dye-fixing agents, anti-bacterial agents and anti-fungal agents. The fragrances or perfumes may be encapsulated, e.g. in latex microcapsules or gelatine based coacervates.

Suitable examples of bleaches are photobleaches. Examples of photobleaches are given in EP-A-379 312 (British Petroleum), which discloses a water-insoluble photobleach derived from anionically substituted porphine, and in EP-A-035 470 (Ciba Geigy), which discloses a textile treatment composition comprising a photobleaching component.

Another advantage of the present invention is that it is possible to target some benefit molecules to particular regions of fabric. For example, dyes can be targeted to colour-bleached regions to replenish dye lost in the main wash or fragrance can be targeted to regions where it is most needed, in particular to those regions where microbes associated with malodour are present, such as the "underarm" regions.

1.3 The Fabrics

For laundry detergent applications, several classes of natural or man-made fabrics can be envisaged, in particular cotton. In the embodiment of the invention whereby the antibody region of the fusion protein targets the fabric, such macromolecular compounds have the advantage that they can have a more immunogenic nature, i.e. that it is easier to raise antibodies against them. Furthermore, they are more accessible at the surface of the fabric than for instance coloured substances in stains, which generally have a low molecular weight.

An important embodiment of the invention is to use binding domains (as described above) that bind to several different types of fabrics. This would have the advantage of enabling a Benefit Agent to be deposited to several different types of fabric using the CBD-antibody fusion molecule.

2. The Detergent Composition.

The fusion proteins of the invention can be used in a detergent composition which is specifically suited for the purpose, and this constitutes a second aspect of the invention. When formulating a detergent composition, it is important to ensure that the other ingredients of the product are compatible with the activity of the fusion protein. WO-A-98/07820 (P&G) discloses inter alia rinse treatment compositions containing antibodies directed at cellulase and standard softener actives such as DEQA. The detergent product according to the present invention preferably contains no softener or low levels of softener active (e.g. HEQ).

To that extent, the detergent composition comprises one or more benefit agents and optionally other conventional detergent ingredients. The invention in its second aspect provides a detergent composition which comprises from 0.1–50% by weight, based on the total composition, of one or more surfactants. This surfactant system may in turn comprise 0–95% by weight of one or more anionic surfactants and 5–100% by weight of one or more nonionic surfactants. The surfactant system may additionally contain amphoteric or zwitterionic detergent compounds, but this in not normally desired owing to their relatively high cost. It may be be advantageous to also include cationic surfactants into the composition. Examples of suitable cationic surfactants are given in WO-A-97/03160 and WO-A-98/17767 (Procter&Gamble).

In general, the nonionic and anionic surfactants of the surfactant system may be chosen from the surfactants described "Surface Active Agents" Vol. 1, by Schwartz & Perry, Interscience 1949, Vol. 2 by Schwartz, Perry & Berch, Interscience 1958, in the current edition of "McCutcheon's Emulsifiers and Detergents" published by Manufacturing Confectioners Company or in "Tenside-Taschenbuch", H. Stache, 2nd Edn., Carl Hauser Verlag, 1981.

Suitable nonionic detergent compounds which may be used include, in particular, the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are $C_6$–$C_{22}$ alkyl phenol-ethylene oxide condensates, generally 5 to 25 EO, i.e. 5 to 25 units of ethylene oxide per molecule, and the condensation products of aliphatic $C_8$–$C_{18}$ primary or secondary linear or branched alcohols with ethylene oxide, generally 5 to 40 EO.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulphates, especially those obtained by sulphating higher $C_8$–$C_{18}$ alcohols, produced for example from tallow or coconut oil, sodium and potassium alkyl $C_9$–$C_{20}$ benzene sulphonates, particularly sodium linear secondary alkyl $C_{10}$–$C_{15}$ benzene sulphonates; and sodium alkyl glyceryl ether sulphates, especially those ethers of the higher alcohols derived from tallow or coconut oil and synthetic alcohols derived from petroleum. The preferred anionic detergent compounds are sodium $C_{11}$–$C_{15}$ alkyl benzene sulphonates and sodium $C_{12}$–$C_{18}$ alkyl sulphates. Also applicable are surfactants such as those described in EP-A-328 177 (Unilever), which show resistance to salting-out, the alkyl polyglycoside surfactants described in EP-A-070 074, and alkyl monoglycosides.

Preferred surfactant systems are mixtures of anionic with nonionic detergent active materials, in particular the groups and examples of anionic and nonionic surfactants pointed out in EP-A-346 995 (Unilever). Especially preferred is surfactant system which is a mixture of an alkali metal salt of a $C_{16}$–$C_{18}$ primary alcohol sulphate together with a $C_{12}$–$C_{15}$ primary alcohol 3–7 EO ethoxylate.

The nonionic detergent is preferably present in amounts greater than 10%, e.g. 25–90% by weight of the surfactant system. Anionic surfactants can be present for example in amounts in the range from about 5% to about 40% by weight of the surfactant system.

The detergent composition may take any suitable physical form, such as a powder, a tablet, an aqueous or non aqueous liquid, a paste or a gel. The fusion protein according to the invention will generally be used as a dilution in water of about 0.05 to 2%.

The detergent composition in accordance with the invention comprising the fusion protein can have any suitable form, i.e. the form of a granular composition, a liquid or a slurry of the enzyme, or with carrier material (e.g. as in EP-A-258 068 and the Savinase™ and Lipolase™ products of Novo Nordisk). A good way of adding the fusion protein to a liquid detergent product is in the form of a slurry containing from 0.005 to 50% by weight of the complex in an ethoxylated alcohol nonionic surfactant.

The detergent compositions of the invention comprise about 0.001 to 50 mg, preferably from 0.01 to 10 mg of fusion protein per liter of the rinse liquor in use. A concentrated detergent composition before use will comprise about 1 to 1000 mg/l, preferably from 10 mg to 100 mg per liter of the detergent product.

The invention will now be further illustrated in the following, non-limiting Examples.

EXAMPLE 1

CBD-anti *Streptococcus sangius* Fusion
(CBD-4715)

The ability of the CBD-fusion to capture bacteria onto a cellulosic matrix was investigated. The following protocol describes the method used to crosslink bacteria to cellulose via a CBD-antibody crosslinker, whereby the CBD region bound to the cellulose and the antibody domain binds to the bacteria: 1% phosphoric acid swollen cellulose was used to which 0–500 µl 0.1 mg/ml CBD-4715 was added and volume made to 1 ml with PBS pH 7. The samples were incubated for 30 minutes on a end over end shaker at 25° C. After each incubation step the samples were washed. To each tube 100 µl $2.56 \times 10^8$ *Streptococcus sangius* cells were added. Resulting samples were mixed for 10 minutes and then the samples were centrifuged and washed in PBS. An aliquot of each solution was removed and 10 µl 0.1 mg/ml carboxyfluorescein diacetate was added. This is a fluorescent marker for viable bacterial cells. Captured bacteria were visualised by green fluorescence (Excitation 488 nm, Emission 525 nm). In the presence of the CBD fusion, bacteria were specifically captured onto the cellulosic material. This was in stark contrast to samples in the absence of the crosslinker, whereby bacteria were not associated with the cellulosic.

EXAMPLE 2

Latex Capture on Cellulose Fibres (CBD-anti HCG Fusion)

The ability of the CBD-anti HCG fusion to capture latex particles onto cotton yarns was tested: cotton yarns were washed thoroughly in 0.5 ml 0.1M sodium carbonate pH 9.0. To these 0–12 µl 0.4 mg/ml CBD-anti HCG fusion was added and incubated at 25° C. for 10 minutes. The supernatants were removed and the yarns washed in 0.1M sodium carbonate pH 9.0. Yarns were then resuspended in 0.1M sodium carbonate pH 9.0 containing 0.25% Tween. 0–15 µl duke green-HCG latex was added and samples were then incubated at 25° C. for 20 minutes. Yarns were then washed with PBS-Tween and the yarns removed and dried. Latex remaining on the yarns was identified by fluorescence.

Single cotton yarns were used as the target surface. The incorporation of Tween was essential to remove the non-specific entrapment of latex on cotton. There was a good correlation between CBD fusion dose and degree of particle capture. This correlation is described in the following table:

|  | μl CBD Fusion | | | |
| --- | --- | --- | --- | --- |
|  | 0 | 4 μ | 8 μl | 12 μl |
| 0 μl latex | – | – | – | – |
| 5 μl latex | – | + | + | +++ |
| 10 μl latex | – | ++ | ++ | +++ |
| 15 μl latex | – | +++ | ++++ | +++++ |

Scale:
– = No capture of latex onto cotton
++ = Capture of latex onto cotton clearly visible
+++++ = Significant capture of latex onto cotton

EXAMPLE 3

Capture of Coacervate Particles Containing a Model Benefit Agent onto Fabric Via a CBD-antibody Fusion Protein Crosslinker The next step was to investigate the ability to capture coacervate microcapsules onto cotton fabric using a CBD-fusion. The benefit agent in the capsule to be delivered was sunflower oil/β-carotene sample as a model. Coacervate particles allow the incorporation of many hydrophobic and insoluble molecules. There was clear indication of enhanced deposition of particles to fabric, and the qualitative data produced suggested a dose response with the concentration of fusion protein. The untreated fabric did show entrapment of particles but there was a considerable increase in the delivery and deposition of capsules in the presence of the fusion protein. This correlation is shown in the following table:

| mg CBD Fusion | 0 | 0.05 | 0.125 |
|---|---|---|---|
| Capture | + | ++++ | +++++ |

Scale:
+ = Capture of coacervates onto cotton visible
+++++ = Significant capture of coacervates onto cotton.

EXAMPLE 4

Production of the Fusion Protein

To demonstrate the feasibility of the concept we have combined an existing llama antibody gene sequence (anti-Reactive Red 6) with a CBD sequence to produce a single fusion protein. In this manner, we have put Reactive Red 6 dye onto perfume particles and show the deposition using the fusion proteins. It will be clear that we can generate any molecule of choice for the antibody region e.g. an anti-gelatine coacervate specificity.

The antibody gene which conferes binding to the dye Reactive Red 6 was combined with a CBD gene (taken from *Tricoderma reesei*) with a small peptide linker in between the two sequences. The combination of the two genes was performed via convention molecular biology techniques. To demonstrate that the gene was successfully produced, the sequence of the expressed fusion protein is shown in FIG. 1.

The vector containing the selected anti-Reactive Red 6 Vhh-CBD-gene was then used to transfer cells for a larger scale production of the fusion protein. From a 5 liter fermentation broth 60 mg/l fusion protein was isolated.

1.1 Perfumed Latex Particles.

Positively charged latex containing perfume fragrance was derivatised with 0.1% Reactive Red 6. Binding to the dye was effective by incubation in 0.1 M sodium borohydrate buffer/0.05 M NaCl for 2 hours. Resulting latex particles were spun and washed to remove any free dye.

1.2 Coacervate Particles

Coacervate particles were constructed via the simple coacervation method: 3 gm gum arabic disssolved in 100 ml water and maintained at 40° C. To this solution 0.5 ml perfume was added and an emulsion was formed using a polytron. This solution was mixed with 100 ml gelatine (also at 40° C). The pH of the resulting solution was reduced to pH 4 using 1M HCl. Sample was left to stir at room temperature and finally chilled on ice for 2 hours. The resulting particles were then derivatised with Reactive Red 6 as described for the latex particles (section 1.1).

EXAMPLE 5

Binding Perfumed Latex Particles to Cotton

Assay: 100 μl 0.1% Reactive Red 6 coated perfume latex was added to a reaction vial in a total volume of 5 ml. This contained 50 mM HEPES buffer and 200 μl PBST. The solution also contained either no CBD fusion or 200 μg CBD-anti Reactive Red 6 protein.

Solutions were mixed for 30 minutes at room temperature. Cotton strands (2×3 cm—prewashed in buffer) were then added to the vials and incubated for a further 30 minutes at room temperature. The cotton strands were then removed and placed into glass vials containing 25 ml water and were rinsed. The resulting strands were then placed into glass vials containing 1ml ethyl acteate and capped. These vials were sonicated and then analysed by GC-MS following specfic perfume components. FIGS. 2 and 3 demonstrate the enhanced binding of perfumed latex in the presence of the fusion protein.

EXAMPLE 6

Binding Perfume Containing Coacervate Particles to Cotton

Assay: 50 μl 0.375% coacervate particles were added to a reaction volume containing 2 ml PBST either in the presence or absence of 100 μg fusion protein. The samples were mixed for 30 minutes prior to the adition of 2 cm cotton yarns. Samples were incubated for a further 30 minutes at room temperature and were rinsed at the end of of this period in 25 ml PBST. The cotton strands were then added to glass vials containing 1ml ethyl acetate and were incubated at 50° C. for 30 minutes and sonicated. Perfume components of the encapsulated perfume were then analysed by GC-MS. FIGS. 3 and 4 below clearly demonstrate the enhanced level of perfume deposition using this novel cross linking fusion protein approach.

The invention claimed is:

1. Detergent composition comprising:
   a) a surfactant; and
   b) a fusion protein comprising a cellulose binding domain and a domain having a high binding affinity for another ligand, with chemical equilibrium constant $K_D$ for binding between the domain having the high binding activity and the ligand being lower than $10^{-4}$M,
   wherein the domain having a high binding affinity is an antibody or antibody fragment and,
   wherein the domain having a high binding affinity binds to one of the following: a benefit agent selected from the group consisting of softening agents, finishing agents/protective agents, fragrances, bleaching agents and dyes, a fabric, a specific part of the fabric, or micro-particles which are loaded with a benefit agent.

2. The detergent composition of claim 1, wherein the cellulose binding domain is obtained from a fungal enzyme isolated from fungi selected from the group consisting of *Humicola, Trichoderma, Thermomonospora, Phanerochaete* and *Aspergillus* or from a bacterial enzyme isolated from bacteria origin selected from the group consisting of *Bacillus, Clostridimum, Streptomyces, Cellulomonas* and *Pseudomonas*.

3. The detergent composition of claim 1, wherein the cellulose binding domain of the fusion protein is obtained from *Trichoderma reesei*.

4. The detergent composition of claim 1, wherein the antibody is a heavy chain antibody as found in Camelidae or obtained from $V_h$ fragments by a camelization procedure.

5. The detergent composition of claim 1, wherein the benefit agent is selected from the group consisting of fabric softening agents, fragrances, perfumes, polymeric lubercants, photoprotective agents, latexes, resins, dye fixative agents, antioxidants, insecticides, soil repelling agents and soil release agents.

6. The detergent composition of claim 1, wherein the cellulose binding domain of the fusion protein is connected to the domain having a high binding affinity for another ligand by means of a linker consisting of 2–15 amino acids.

7. The detergent composition of claim 1, wherein the antibody or the antibody fragment is multi-specfic.

8. Process for delivering a benefit agent to a fabric by treating the fabric with a composition comprising:
   a) a fusion protein comprising a cellulose binding domain and a domain having a high binding affinity for another ligand, with chemical equilibrium constant $K_D$ for binding between the domain having the high binding activity and the ligand being lower than $10^{-4}$M,
   wherein the domain having a high binding affinity is an antibody or antibody fragment and,
   wherein the domain having a high binding affinity binds to one of the following: a benefit agent, a fabric, a specific part of the fabric, or micro-particles which are loaded with a benefit agent: and
   b) a benefit agent selected from the group consisting of softening agents, finishing agents/protective agents, fragrances and bleaching agents.

* * * * *

SEQUENCE LISTING

<160> NUMBER OF SEQ ID NOS: 2

<210> SEQ ID NO 1
<211> LENGTH: 558
<212> TYPE: DNA
<213> ORGANISM: Trichoderma reesei
<220> FEATURE:
<221> NAME/KEY: CDS
<222> LOCATION: (3)..(551)

<400> SEQUENCE: 1

```
tc gag aaa aga cag gtg cag ctg cag gag tca ggg gga gga ttg gtg         47
   Glu Lys Arg Gln Val Gln Leu Gln Glu Ser Gly Gly Gly Leu Val
   1               5                  10                 15 cag gct ggg ggc tct ctg aga ctc tcc tgt gca gcc tcg gga cgc gcc        95
Gln Ala Gly Gly Ser Leu Arg Leu Ser Cys Ala Ala Ser Gly Arg Ala
                20                  25                  30 acc agt ggt cat ggt cac tat ggt atg ggc tgg ttc cgc cag gtt cca       143
Thr Ser Gly His Gly His Tyr Gly Met Gly Trp Phe Arg Gln Val Pro
            35                  40                  45 ggg aag gag cgt gag ttt gtc gca gct att agg tgg agt ggt aaa gag       191
Gly Lys Glu Arg Glu Phe Val Ala Ala Ile Arg Trp Ser Gly Lys Glu
        50                  55                  60 aca tgg tat aaa gac tcc gtg aag ggc cga ttc acc atc tcc aga gat       239
Thr Trp Tyr Lys Asp Ser Val Lys Gly Arg Phe Thr Ile Ser Arg Asp
    65                  70                  75 aac gcc aag act acg gtt tat ctg caa atg aac agc ctg aaa cct gaa       287
Asn Ala Lys Thr Thr Val Tyr Leu Gln Met Asn Ser Leu Lys Pro Glu
80                  85                  90                  95 gat acg gcc gtt tat tat tgt gcc gct cga ccg gtc cgc gtg gat gat       335
Asp Thr Ala Val Tyr Tyr Cys Ala Ala Arg Pro Val Arg Val Asp Asp
                100                 105                 110 att tcc ctg ccg gtt ggg ttt gac tac tgg ggc cag ggg acc cag gtc       383
Ile Ser Leu Pro Val Gly Phe Asp Tyr Trp Gly Gln Gly Thr Gln Val
            115                 120                 125 acc gtc tcc tca gga tct cat cac cat cac cat cac gga tcc acc tcc       431
Thr Val Ser Ser Gly Ser His His His His His His Gly Ser Thr Ser
        130                 135                 140 att gaa ggt cgt acc cag tct cac tac ggt cag tgt ggt ggt att ggt       479
Ile Glu Gly Arg Thr Gln Ser His Tyr Gly Gln Cys Gly Gly Ile Gly
    145                 150                 155 tac tcc ggt cca acc gtc tgt gcc tct ggt acc acc tgt cag gtt ctg       527
Tyr Ser Gly Pro Thr Val Cys Ala Ser Gly Thr Thr Cys Gln Val Leu
160                 165                 170                 175 aac cct tac tac tcc cag tgt ctg taataag                               558
Asn Pro Tyr Tyr Ser Gln Cys Leu
                180
```

<210> SEQ ID NO 2
<211> LENGTH: 183
<212> TYPE: PRT
<213> ORGANISM: Trichoderma reesei

<400> SEQUENCE: 2

```
Glu Lys Arg Gln Val Gln Leu Gln Glu Ser Gly Gly Gly Leu Val Gln
1               5                   10                  15

Ala Gly Gly Ser Leu Arg Leu Ser Cys Ala Ala Ser Gly Arg Ala Thr
            20                  25                  30

Ser Gly His Gly His Tyr Gly Met Gly Trp Phe Arg Gln Val Pro Gly
        35                  40                  45
```

-continued

```
Lys Glu Arg Glu Phe Val Ala Ala Ile Arg Trp Ser Gly Lys Glu Thr
    50                  55                  60

Trp Tyr Lys Asp Ser Val Lys Gly Arg Phe Thr Ile Ser Arg Asp Asn
65              70                  75                      80

Ala Lys Thr Thr Val Tyr Leu Gln Met Asn Ser Leu Lys Pro Glu Asp
            85                  90              95

Thr Ala Val Tyr Tyr Cys Ala Ala Arg Pro Val Arg Val Asp Asp Ile
            100             105             110

Ser Leu Pro Val Gly Phe Asp Tyr Trp Gly Gln Gly Thr Gln Val Thr
        115             120             125

Val Ser Ser Gly Ser His His His His His Gly Ser Thr Ser Ile
    130             135             140

Glu Gly Arg Thr Gln Ser His Tyr Gly Gln Cys Gly Gly Ile Gly Tyr
145             150             155             160

Ser Gly Pro Thr Val Cys Ala Ser Gly Thr Thr Cys Gln Val Leu Asn
            165             170             175

Pro Tyr Tyr Ser Gln Cys Leu
            180
```